(12) United States Patent
Tisdale et al.

(10) Patent No.: US 6,890,899 B1
(45) Date of Patent: May 10, 2005

(54) GLYCOPROTEINS HAVING LIPID MOBILIZING PROPERTIES AND THERAPEUTIC APPLICATIONS THEREOF

(76) Inventors: Michael J Tisdale, Wellcot, Star Lane, Claverdon, Warwickshire CV35 8LW (GB); Penio T Todorov, 9 Mattock Way, Abingdon, Oxfordshire OX14 2PB (GB)

( * ) Notice: Subject to any disclaimer, the term of this patent is extended or adjusted under 35 U.S.C. 154(b) by 0 days.

(21) Appl. No.: 09/701,463

(22) PCT Filed: Jun. 1, 1999

(86) PCT No.: PCT/GB99/01509

§ 371 (c)(1),
(2), (4) Date: May 2, 2001

(87) PCT Pub. No.: WO99/62939

PCT Pub. Date: Dec. 9, 1999

(30) Foreign Application Priority Data

May 29, 1998 (GB) .............................. 9811465

(51) Int. Cl.⁷ .............................. A61K 38/16
(52) U.S. Cl. .......................................... 514/8
(58) Field of Search .................. 514/8, 2, 12; 530/350, 530/380

(56) References Cited

PUBLICATIONS

Araki et al. Complete amino acid sequence of human Zn–alpha 2–glycoprotein and its homology to histocompatibility antigens. Proc Natl Acad Sci U S A. Feb. 1988;85(3):679–83.*

Ohkubo et al. Purification and characterization of human plasma Zn–alpha 2–glycoprotein. Prep Biochem. 1988;18(4):413–30.*

Hirai et al. Biological evaluation of a lipid–mobilizing factor isolated from the urine of cancer patients. Cancer Res. Jun. 1, 1998;58(11):2359–65.*

Sanchez et al: "Biochemical characterization and crystallization of human Zn–alpha2–glycoprotein, a soluble class I major histocompatibility complex homolog", Proceedings of the National Academy of Sciences of USA, vol 94, no 9, Apr. 29, 1997, pp. 4626–4630, XP002127900, ISSN: 0027–8424.

Kitada et ak: "Characterization of a lipid mobilizing factor from tumors", Chemical Abstracts, vol 96, no 21, May 24, 1982, abstract no 178891, XP002127902, & Prog. Lipid Res., vol 20, no 1–4, 1981, pp. 823–826.

Todorov et al: "Purification and characterization of a tumor lipid–mobilizing factor", Cancer Research, vol 58, Jun. 1, 1998, pp. 2353–2358, XP002127901, ISSN: 0027–8424.

* cited by examiner

*Primary Examiner*—Karen Cochrane Carlson
*Assistant Examiner*—Sheridan K Snedden
(74) *Attorney, Agent, or Firm*—Pillsbury Winthrop LLP

(57) ABSTRACT

A biologically active lipid mobilizing agent for use in therapy is disclosed which has the properties and characteristics of a Zn-$\alpha_2$-glycoprotein, or of a fragment thereof having an apparent molecular mass $M_r$ greater than 6.0 kDa as determined by gel exclusion chromatography. Methods of isolation and purification from biological material are also disclosed together with uses of the material for making up pharmaceutical compositions, especially pharmaceutical compositions useful for treating mammals to achieve weight reduction or for controlling obesity. In addition, uses of the material for developing diagnostic agents and for identifying inhibitors of lipolytic activity for therapeutic purposes are disclosed.

2 Claims, 10 Drawing Sheets

FIG. 1 (SEQ ID NO:1)

Gln Glu Asn Gln Asp Gly Arg Tyr Ser Leu Thr
Tyr Ile Tyr Thr Gly Leu Ser Lys His Val Glu
Asp Val Pro Ala Phe Gln Ala Leu Gly Ser Leu
Asn Asp Leu Gln Phe Phe Arg Tyr Asn Ser Lys
Asp Arg Lys Ser Gln Pro Met Gly Leu Trp Arg
Gln Val Glu Gly Met Glu Asp Trp Lys Glu Asp
Ser Gln Leu Gln Lys Ala Arg Glu Asp Met Glu
Thr Leu Lys Asp Ile Val Glu Tyr Tyr Asn Asp
Ser Asn Gly Ser His Val Leu Gln Gly Arg Phe
Gly Cys Glu Ile Glu Asn Asn Arg Ser Ser Gly
Ala Phe Trp Lys Tyr Tyr Tyr Asp Gly Lys Asp
Tyr Ile Glu Phe Asn Lys Glu Ile Pro Ala Trp
Val Pro Phe Asp Pro Ala Ala Gln Ile Thr Lys
Gln Lys Trp Glu Ala Glu Pro Val Tyr Val Gln
Arg Ala Lys Ala Tyr Leu Glu Glu Glu Cys Pro
Ala Thr Leu Arg Lys Tyr Leu Lys Tyr Ser Lys
Asn Ile Leu Asp Arg Gln Asp Pro Pro Ser Val
Val Val Thr Ser His Gln Ala Pro Gly Glu Lys
Lys Lys Leu Lys Cys Leu Ala Tyr Asp Phe Tyr
Pro Gly Lys Ile Asp Val His Trp Thr Arg Ala
Gly Gln Val Gln Glu Pro Glu Leu Arg Gly Asp
Val Leu His Asn Gly Asn Gly Thr Tyr Gln Ser
Trp Val Val Val Ala Val Pro Pro Gln Asp Thr
Ala Pro Tyr Ser Cys His Val Gln His Ser Ser
Leu Ala Gln Pro Leu Val Val Pro Trp Glu Ala
Ser COOH

GLYCOPROTEINS HAVING LIPID MOBILIZING PROPERTIES AND THERAPEUTIC APPLICATIONS THEREOF

The above patent application is the U.S. National Stage of PCT/GB99/01509, filed Jun. 1, 1999, which claims priority from Great Britain Patent Application No. 9811465.5, filed May 29, 1998, both of which are incorporated herein in their entirety by reference.

FIELD OF THE INVENTION

This invention relates to the field of biochemistry and medicine and it is especially concerned with therapeutic applications of certain glycoproteins, including fragments thereof, which exhibit lipid mobilising properties in biological systems. In particular, in one aspect the invention embraces the use of such glycoproteins and fragments thereof for therapeutic treatment of mammals to achieve a weight reduction or for controlling obesity. The invention also relates to the isolation and purification of such glycoproteins from biological material. The invention also relates to the use of such glycoproteins for developing diagnostic agents and inhibitors for therapeutic use.

BACKGROUND

For convenience, reference publications relating to or mentioned in the following description are numerically labelled and listed in the appended bibliography.

The invention has its origins in research carried out in connection with cancer cachexia. Cancer cachexia is a common condition in many human cancer patients, especially patients with gastrointestinal or lung cancer, and is characterised by progressive weakness, dramatic weight loss and wasting resulting from loss of both adipose tissue and skeletal muscle mass. Previous investigations have indicated that the characteristic loss of weight and body issues (fat and muscle) cannot usually be explained simply by a reduction of food and water intake, and the effect has been attributed to production by the tumours of catabolic factors that pass into the circulatory system. Both lipolytic and proteolytic activities are involved, and there have been numerous attempts to isolate and purify the substances that produce these activities, especially lipid mobilising factors responsible for the catabolism of adipose tissue and reduction of carcass fat.

In GB2217330A, for example, the supposed isolation and purification was described of lipolytic factors derived from a cachexia-inducing murine tumour designated MAC16 and also from the urine of cachectic cancer patients using chromatographic methods which included at least one stage of gel filtration exclusion chromatography, and results were obtained that suggested there were several related molecular species having an apparent molecular weight less than 5000 daltons that were responsible for the lipolytic effect. Severe problems were encountered, however, in attempting to purify the active molecular species to the extent required for use in therapeutic applications and fully to characterise the active material in terms of its chemical constitution. More recently, in 1995, a paper by T. M. McDevitt et al., entitled "Purification and characterisation of a lipid-mobilising factor associated with cachexia-inducing tumours in mice and humans", was published in Cancer Research 55, 1458–1463 (reference 1), wherein it was reported that a material having an apparent relative molecular mass $M_r$ of 24 kDa had been isolated from both the above-mentioned cachexia-inducing murine tumour MAC16 and from the urine of patients with cancer cachexia using an isolation and purification procedure involving a combination of ion exchange, size exclusion and hydrophobic chromatography, and a belief was expressed that this material was a purified form of cancer cachexia lipid mobilising factor. It was subsequently found, however, that this 24 kDa material was in fact a proteoglycan which when purified to homogeneity would produce a cachectic state in non-tumour bearing mice by inducing catabolism of skeletal muscle protein, as reported by P. Todorov et al. 1996, Nature, 379, 739–742 (reference 2). Thus, this 24 kDa material was a proteolytic factor and it seems that any lipolytic activity had to be attributed to contamination through co-purification with a separate and distinct lipolytic factor.

SUMMARY OF THE INVENTION

The present invention is based on the subsequent finding that a true lipolytic or lipid mobilising factor (LMF) produced by the cachexia-inducing murine tumour MAC16 and present also in urine of cancer cachexia patients is in fact a glycoprotein which has an apparent relative molecular weight of about 43 kDa as determined by its electrophoretic mobility when subjected to 15% SDS-PAGE electrophoresis and which is the same as, or which is very similar to and has characteristics in common with, a glycoprotein known as Zn-$\alpha_2$-glycoprotein. Zn-$\alpha_2$-glycoprotein has been known since it was found in human blood plasma and first reported in a paper by Burgi and Schmid entitled "Preparation and properties of Zn-$\alpha_2$-glycoprotein of normal human plasma" (1961) J. Biol. Chem. 236, 1066–1074 (reference 3). Although the properties and physiological function of this material have not been fully determined, the material has been highly purified and characterised in terms of chemical and physical chemical properties. Moreover, the complete amino acid sequence has been reported in a paper entitled "Complete amino acid sequence of human plasma Zn-$\alpha_2$-glycoprotein and its homology to histocompatibility antigens" by T. Araki et al. (1988) Proc. Natl. Acad. Sci. USA., 85, 679–683 (reference 4) wherein the glycoprotein was shown as consisting of a single polypeptide chain of 276 amino acid residues having three distinct domain structures (A, B and C) and including two disulfide bonds together with N-linked glycans at three glycosylation sites. This amino acid sequence of the polypeptide component is set out in FIG. 1 of the accompanying drawings. Although some subsequent publications have indicated that the composition of human Zn-$\alpha_2$-glycoprotein can vary somewhat when isolated from different body fluids or tissues, all preparations of this material have substantially the same immunological characteristics. As reported by H. Ueyama, et al. (1991) "Cloning and nucleotide sequence of a human Zn-$\alpha_2$-glycoprotein cDNA and chromosomal assignment of its gene", Biochem. Biophys. Res. Commun. 177, 696–703 (reference 5), cDNA of Zn-$\alpha_2$-glycoprotein has been isolated from human liver and prostate gland libraries, and also the gene has been isolated, as reported by H. Ueyama et al. (1993) "Molecular cloning and chromosomal assignment of the gene for human Zn-$\alpha_2$-glycoprotein", Biochemistry 32, 12968–12976 (reference 6). H. Ueyama et al. have also described, in J. Biochem. (1994) 116, 677–681 (reference 7), studies on Zn-$\alpha_2$-glycoprotein cDNA's from rat and mouse liver which, together with the glycoprotein expressed by the corresponding mRNA's, have been sequenced and compared with the human material. Although detail differences were found as would be expected from different species, a high degree of amino acid sequence homology was found with over 50% identity with the human counterpart (over 70% identity within domain B of the glycoprotein). Again, common immunological properties between the human, rat and mouse Zn-$\alpha_2$-glycoproteins have been observed.

The preparation of purified Zn-$\alpha_2$-glycoprotein from fresh human plasma by a method involving six steps of column chromatography separation has been described by Ohkubo et al. in a paper entitled "Purification and characterisation of human plasma Zn-$\alpha_2$-glycoprotein" (1988) *Prep. Biochem.*, 18, 413–430 (reference 8), of which the content is incorporated herein by reference.

The 43 kDa glycoprotein lipolytic or lipid mobilising factor (LMF) isolated and purified in connection with the present invention has been obtained substantially free of any proteolytic factor, both from the cachexia inducing murine tumour MAC16 and from urine of patients with cancer cachexia, using an improved isolation and purification procedure. This procedure has again involved a combination of ion exchange, exclusion and hydrophobic chromatographic separations but the selectivity of the separations differs from that of chromatographic separations previously used when the 24 kDa cachectic factor was isolated, yielding a product that when subjected to 15% SDS-PAGE electrophoresis shows a single band of apparent relative molecular weight of about 43 kDa. As already indicated, the lipolytic active material or lipid mobilising factor (LMF) thus isolated, from both the MAC16 tumour and from cancer patients' urine, has been found to be a glycoprotein with characteristics in common with or the same as those of Zn-$\alpha_2$-glycoprotein isolated from human plasma. Accordingly it has been concluded that this human and mouse LMF are both Zn-$\alpha_2$-glycoproteins or are very close analogues thereof having a substantial degree of sequence homology and substantially the same biological activity, especially in relation to lipolytic activity with respect to adipocytes. They may therefore be referred to as glycoproteins of the Zn-$\alpha_2$-glycoprotein type.

In particular, it has been found that:

a) the human and mouse lipid mobilising factors which have been isolated from the above-mentioned sources both co-migrated with authentic human plasma Zn-$\alpha_2$-glycoprotein on 15% SDS-PAGE and on 10% non-denaturing gels;

b) the human and mouse lipid mobilising factors isolated both stained heavily for carbohydrates in the same way as authentic Zn-$\alpha_2$-glycoprotein;

c) a polyclonal antibody against human plasma Zn-$\alpha_2$-glycoprotein was capable of detecting the lipid mobilising activity of the human material and of neutralising this activity in vitro;

d) authentic human plasma Zn-$\alpha_2$-glycoprotein also shows in vitro lipid mobilising activity and also stimulates adenylate cyclase activity;

e) the human and mouse lipid mobilising factor and the authentic human Zn-$\alpha_2$-glycoprotein each show the same chymotrypsin digestion pattern producing similar fragments and loss of activity;

f) the human lipid mobilising factor isolated is homologous with authentic human plasma Zn-$\alpha_2$-glycoprotein in amino acid sequence and both have been shown to stimulate production of adenylate cyclase in murine adipocyte plasma membranes in a GTP-dependent process with maximum stimulation at 0.1 $\mu$MGTP.

The term authentic Zn-$\alpha_2$-glycoprotein is used herein to denote purified Zn-$\alpha_2$-glycoprotein as prepared from fresh human plasma substantially according to the method described by Ohkubo et al. (reference 8). It will be appreciated that in some cases fragments of the isolated lipid mobilising factor or of authentic Zn-$\alpha_2$-glycoprotein may be produced without loss of the lipolytic or lipid mobilising activity, and various additions, deletions or substitutions may be made which also will not substantially affect this activity. In that aspects of the present invention relate to therapeutic applications, it is however important that a high degree of purity should generally be achieved and, in particular, the material should be substantially free of proteolytic activity.

In one aspect, the present invention relates to the use in medicine of a glycoprotein lipid mobilising factor as herein defined or a therapeutically effective fragment derived therefrom for treatment of conditions of overweight or obesity in mammals.

More particularly, the invention provides a biologically active lipid mobilising agent for use in therapy characterised in that it has the properties and characteristics of a Zn-$\alpha_2$-glycoprotein, or of a fragment of a Zn-$\alpha_2$-glycoprotein that has an apparent molecular mass $M_r$, as determined by gel exclusion chromatography, greater than 6.0 kDa. In preferred embodiments this lipid mobilising agent can be defined as being a glycosylated polypeptide wherein the polypeptide moiety is selected from one of the following groups:

(a) a polypeptide having the amino acid sequence of a Zn-$\alpha_2$-glycoprotein;

(b) a polypeptide which in respect to (a) is deficient in one or more amino acids;

(c) a polypeptide in which in respect to (a) one or more amino acids are replaced by a different amino acid or acids;

(d) a polypeptide in which in respect to (a) there is a plurality of additional amino acids which do not interfere with the biological lipolytic activity or which may be readily eliminated;

(e) a polypeptide which is an allelic derivative of a polypeptide according to (a).

Also according to the invention, a biologically active lipid mobilising agent for use in therapy consists essentially of a glycoprotein, or a fragment of said glycoprotein that has an apparent relative molecular mass $M_r$, as determined by gel exclusion chromatography, greater than 6 kDa, said glycoprotein being characterised in that it has a polypeptide amino acid sequence that is homologous with the amino acid sequence (SEQ ID No: 1) of human plasma Zn-$\alpha_2$-glycoprotein, or with a variant thereof which is modified by additions, deletions, or substitutions that do not substantially affect its lipid mobilising activity in biological systems.

In at least some embodiments of the invention the lipid mobilising agent may be further characterised by an apparent relative molecular mass $M_r$ of about 43 kDa as determined by its electrophorectic mobility when subjected to 15% SDS-PAGE electrophoresis.

Thus, also according to the invention, a purified biologically active lipid mobilising agent for use in therapy is characterised in that it consists essentially of a glycosylated polypeptide comprising a single main component having an apparent relative molecular mass $M_r$ of about 43 kDa as determined by its electrophoretic mobility when subjected to 15% SDS-PAGE electrophoresis and having homology in amino acid sequence with the amino acid sequence (SEQ ID No: 1) of human plasma Zn-$\alpha_2$-glycoprotein. This lipid mobilising agent may be further characterised in some embodiments by the fact that it can be obtained by a process that includes sequential steps of subjecting biological material to ion exchange chromatography, exclusion chromatography, and then to hydrophobic interaction chromatography, wherein said biological material is a body fluid of a cancer cachexia patient or an extract of a culture of a MAC16 tumour cell line deposited in the name of Michael John Tisdale under the provisions of the Budapest Treaty in the European Collection Of Animal Cell Cultures (ECACC) ) at the Public Health Laboratory Service Centre for Applied Microbiology and Research, Portondown, Salisbury, Wiltshire, United Kingdom, under an Accession No. 89030816.

Also, in at least some embodiments, the lipid mobilising agent of the present invention may be further characterised by one or more of the following features:

(a) when subjected to digestion with chymotrypsin it is fragmented and its lipid mobilising properties are destroyed;

(b) it has the potential in vitro to stimulate adenylate cyclase activity in a guanine triphosphate (GTP) dependent process upon incubation with murine adipocyte plasma membranes;

(c) it has substantially the same immunological properties as human $Zn-\alpha_2$-glycoprotein;

(d) it is an active lipid mobilising fragment of the aforesaid 43 kDa glycoprotein or glycosylated polypeptide obtainable by digesting the latter with trypsin;

(e) it is substantially free of proteolytic activity;

(f) the polypeptide chain of the polypeptide component has an N-terminus blocked by a pyroglutamate residue;

(g) the lipid mobilising activity is destroyed by periodate treatment.

The invention also provides pharmaceutical compositions for use in treating mammals, e.g. to reduce their weight or control obesity, said compositions containing as the active constituent an effective therapeutic amount of $Zn-\alpha_2$-glycoprotein or glycoprotein lipid mobilising factor as herein defined, or a lipolytically active fragment thereof, together with a pharmaceutically acceptable carrier, diluent of excipient.

The invention also includes the use of a lipid mobilising agent, as herein defined, for the manufacture of a medicament useful in human medicine for treating conditions of overweight or obesity.

Thus, the invention further provides a glycoprotein lipid mobilising factor having properties and characteristics of $Zn-\alpha_2$-glycoprotein, especially human $Zn-\alpha_2$-glycoprotein, for use in the production of a medicament effective in treating conditions of overweight or obesity. Such a medicament may also be useful for stimulating muscle development and increasing muscle mass.

The invention also provides a method of isolating and purifying lipolytically active glycoprotein or lipid mobilising agent having the properties and characteristics of a $Zn-\alpha_2$-glycoprotein, i.e. a glycoprotein of the $Zn-\alpha_2$-glycoprotein type, said method comprising subjecting an extract of a cachexia-inducing tumour or of a culture of a cachexia-inducing tumour cell line, or a sample of urine or other body fluid from a mammal bearing a cachexia-inducing tumour, to a combination of ion exchange, gel filtration or size exclusion chromatography, and hydrophobic interaction chromatography, yielding a single product or molecular species having an apparent molecular weight or relative molecular mass of 43 kDa, as determined by 15% SDS-PAGE electrophoresis, which is substantially free of proteolytic activity.

The invention also includes a method of treating a mammal to bring about a weight reduction or reduction in obesity, said method comprising administering to the mammal a therapeutically effective dosage of a lipid mobilising agent as herein defined. In general, this will be provided by a glycoprotein identical to or homologous with a human $Zn-\alpha_2$-glycoprotein, or an effective fragment thereof, substantially free of any proteolytic activity.

The lipid mobilising glycoprotein or $Zn-\alpha_2$-glycoprotein may be administered as an injectable formulation incorporating a carrier in the form of a pharmaceutically acceptable injection vehicle.

The glycoprotein or fragment thereof used in these therapeutic applications may further be produced by recombinant DNA techniques such as are well known in the art, based possibly on the known cDNA sequence for $Zn-\alpha_2$-glycoprotein which has been published for example in reference 7.

The invention also includes a method for detecting the presence of a cachexia inducing tumour, and/or for monitoring changes in such a tumour, e.g. during the course of antitumour therapy, said method comprising taking a sample of urine, blood serum or other body fluid, and testing to detect the presence of and/or to measure the amount therein of the lipid mobilising agent herein defined or of $Zn-\alpha_2$-glycoprotein. In carrying out this method, a monoclonal or polyclonal antibody against $Zn-\alpha_2$-glycoprotein or other biochemical reagent may be used as a diagnostic detecting agent, as hereinafter described.

The purified lipid mobilising factor or $Zn-\alpha_2$-glycoprotein of this invention may also be used for producing antibodies, either monoclonal or polyclonal antibodies but preferably monoclonal antibodies, which can then be used as diagnostic detecting agents as mentioned above, or which can be used in therapy as inhibitors or antagonists to the lipolytic agent (s) causing cachexia in cancer patients.

The antibodies referred to may be, for example, whole antibodies or fragments thereof Particular antibody fragments may include those obtained by proteolytic cleavage of whole antibodies, such as $F(ab')_2$, Fab' or Fab fragments; or fragments obtained by recombinant DNA techniques, for example Fv fragments (as described in International Patent Specification No. WO 89/02465. In a further aspect of the invention, the use of one or more of such antibodies is envisaged for the manufacture of a medical preparation or medicament for the treatment of cachexia-associated cancer and/or tumours.

The antibody or antibody fragment may in general belong to any immunoglobulin class. Thus, for example, it may be an immunoglobulin M (IgM) antibody or, in particular, an immunoglobulin G (IgG) antibody. The antibody or fragment may be of animal, for example mammalian, origin and may be for example of murine, rat or human origin. It may be a natural antibody or a fragment thereof, or, if desired, a recombinant antibody or antibody fragment, i.e. an antibody or antibody fragment which has been produced using recombinant DNA techniques.

Particular recombinant antibodies or antibody fragments include, (1) those having an antigen binding site at least part of which is derived from a different antibody, for example those in which the hypervariable or complementary determining regions of one antibody have been grafted into the variable framework regions of a second, different antibody (as described in European Patent Specification No. 239400); (2) recombinant antibodies or fragments wherein non-Fv sequences have been substituted by non-Fv sequences from other, different, antibodies (as described in European Patent Specifications Nos. 171496. 172494 and 194276); or (3) recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody or fragment is in the place of another amino acid residue present in the natural immunoglobulin. (as described in International Patent Specifications Nos. WO 89/01974 and WO 89/01782 respectively).

As indicated, the antibody or antibody fragment may be polyclonal, but is preferably of monoclonal origin. It may be polyspecific, but is preferably monospecific for the lipolytic material or Zn-$\alpha_2$-glycoprotein of the invention.

Whole antibodies may be prepared using well-known immunological techniques employing the purified active lipolytic material or Zn-$\alpha_2$-glycoprotein from any source as antigen. Thus, for example, any suitable host may be injected with the lipolytic material and the serum collected to yield the desired polyclonal antibody after appropriate purification and/or concentration (for example, by affinity chromatography using immobilised lipolytic material as the affinity medium). Alternatively, splenocytes or lymphocytes may be recovered from the injected host and immortalised using for example the method of Kohler et al., (1976), *Eur. J. Immuno*, 6, 511, (reference 9) the resulting cells being segregated to obtain a single genetic line producing monoclonal antibodies in accordance with conventional practice.

If in the above methods the lipolytic material is of a size that does not elicit a suitable immune response in the host, even though it may be antigenic and capable of binding to specific antibodies, it may be preferable covalently to link the material to a large carrier molecule which is itself immunogenic, and to +use the resulting conjugate compound as the antigen, again in accordance with conventional practice [see for example, D. M. Weir, in *"Handbook of Experimental Immunology"*, 3, $2^{nd}$ ed. pp A2.10–A2.11. Blackwell Scientific Publications, Oxford, 1973, (reference 10); and M. Z. Atassi and A. F. S. A. Habeeb, in *"Immunochemistry of Proteins"* (M. Z. Atassi, ed), 2, pp 177–264, Plenum, New York, 1977 (reference 11)].

Antibody fragments may be produced using conventional techniques, for example by enzymatic digestion, e.g. with pepsin [Lanoyi and Nisonoff, (1983) *J. Immunol. Meth.*, 56, 235, (reference 12)]. Where it is desired to produce recombinant antibodies according to the invention these may be produced using for example the general methods described in the above-mentioned patent specifications.

The invention also extends to diagnostic kits for carrying out the diagnostic methods referred to, such kits comprising a receptacle for receiving the sample of body fluid, a biochemical reagent for detecting said lipid mobilising agent or Zn-$\alpha_2$-glycoprotein, and instructions for use of the kit.

The lipid mobilising agent of the present invention may also be used for screening and identifying and/or for carrying out investigations of possible lipolytic activity inhibiting agents having potential as anti-cachectic or antitumour therapeutic agents. This screening may be carried out by adding samples of possible antagonists to, or inhibitors of, the activity of said lipid mobilising agent to preparations of said lipid mobilising agent, followed by incubation in vitro with a preparation of adipocytes and assaying to determine the level of lipolytic activity relative to that of a control sample.

MORE DETAILED DESCRIPTION

Examples hereinafter presented illustrate in more detail at least some aspects of the invention and its development. There first follows, however, an outline or summary of some of the materials, methods and techniques which have generally been used in the development of the invention and in the illustrative examples unless subsequently stated otherwise.

Animals:
Pure strain NEW and ob/ob mice were bred from existing in-house colonies; mate BKW mice (40–50 g) were purchased from Banting and Kingman, Hull, United Kingdom. These animals were transplanted with fragments of the MAC16 tumour into the flanks, by means of a trocar as described by S. A. Beck et al. (1987) "Production of lipolytic and proteolytic factors by a murine tumour-producing cachexia in the host" *Cancer Res*. 47, 5919–5923 (reference 14). The solid tumours were excised from the mice when the weight loss reached 25%.

Subjects:
Urine was collected from patients having unresectable pancreatic cancer with established weight loss ranging between 1.3 and 10 kg/month. These patients were not receiving therapy at the time of urine collection. Samples of urine were stored frozen at –20° C. in the absence of preservatives prior to the purificiation.

Chromatography Apparatus and Materials:
Sephadex™ Mono Q HR 5/5 anionic exchange resin, Superose™ 12H 10/30 gel exclusion and Resource™ Iso hydrophobic chromatography columns were purchased from Pharmacia Biotech, St. Albans, United Kingdom. An Aquapore™ AX-300 DEAE-cellulose column was supplied by Applied Biosystems, California. Rainbow™ protein molecular weight markers, ECL Western blotting system and Hyperfilm™-ECL autoradiography film were from Nycomed Amersham Plc, United Kingdom.

Other Materials:
Other materials included a DIG glycan detection kit from Boehringer Mannheim GmbH, Germany, protein A peroxidase conjugate from Sigma, Dorset, United Kingdom, nitrocellulose membranes from Hoefer Scientific Instruments, California and Amicon filters (YM10) from Amicon Ltd., Stonehouse, Gloucestershire, United Kingdom. Also used were "Mini-Message Maker" and spot-on kits purchased from Rand D Systems, Abingdon, United Kingdom and Superscript™ TH11 RT reverse transcriptase from Gibco BRL, Paisley, Scotland. Oligonucleotides were synthesized by Oswell, Southampton, United Kingdom.

DEAE Cellulose Column Chromatograghy:
In a typical example of using this technique, homogenate containing active lipid mobilising factor (LMF) would be centrifuged and the supernatant would be fractionated by anion exchange chromatography using a DEAE-cellulose column and eluting under a salt gradient. The DEAE-cellulose column would first be equilibrated with buffer solution at the required pH before applying a sample of the material to be fractionated. Thereafter, material would be eluted from the column using a linear salt gradient, e.g. 0 to 0.2M NaCl, in the same buffer. The effluent from the column would be collected in small volume fractions, e.g. 5 ml fractions, and the lipolytic activity of each fraction would be measured by the lipolytic assay technique referred to below.

Use of a DEAE cellulose column with elution under a salt gradient is a procedure at least potentially useful as a preliminary separation stage, but it can be especially useful for obtaining further fractionation after a stage of gel filtration exclusion chromatography and prior to a final or later purification stage of hydrophobic interaction chromatography. As hereinafter described, in a subsequent stage or stages the latter may be carried out employing selected hydrophobic chromatography columns such as Resource™ Iso columns in conjunction with high performance liquid chromatography (HPLC) methods.

Serum Metabolite Determinations

Non-esterified fatty acids (NEFA) were determined using a Wako-ASC-ACOD kit (Wako Chemical GmbH, Neuss, Germany). Triglycerides were determined using a Triglyceride kit (Sigma Chemical Co., Poole, United Kingdom) and 3-hydroxybutyrate by a quantitative enzymatic determination kit (Sigma). Glucose was measured using a glucose analyser (Beckman, Irvine, Calif.) and glycerol was determined enzymatically using the method of Wieland as described in "Methods of Enzymatic Analysis" (Ed. Bergmeyer, H. U.) Vol. 3, pp1404–1409, published by Academic Press, London (1974) (reference 13).

Lipolytic Assay

Single cell suspensions of white adipocytes were prepared from finely minced epididymal fat pads of male BKW mice using collagenase digestion, substantially as described by S. A. Beck et al. (see above-mentioned reference 14). Samples to be assayed were incubated with $10^5$–$2\times10^5$ adipocytes (determined by means of a haemocytometer) for 2 h at 37° C. in 1 ml of Krebs-Ringer bicarbonate buffer, pH 7.2. The concentration of glycerol released was determined enzymatically by the method of Wieland as referred to above (see also GB2217330A). Control samples containing adipocytes alone were analyzed to determine the spontaneous glycerol release. Lipid mobilizing activity was expressed as $\mu$mol glycerol released/$10^5$ adipocytes/2 h.

Isolation of Human Omental Adipocytes

Human omental adipose tissue was removed under general anaesthesia and transported immediately to the laboratory. Fragments of tissue (roughly equivalent in size to a pair of murine epididymal fat pads) were digested to produce a single cell suspension of adipocytes by incubation at 37° C. for 30 min in a 1 ml aliquot of Krebs-Ringer bicarbonate buffer supplemented with 4% bovine serum albumin, 1 g/l glucose and 1.5 mg/ml collagenase, using for this purpose a shaking water bath.

Isolation of Mouse Adipocyte Plasma Membranes

In a typical procedure white adipocytes were isolated from mouse epididymal fat pads as referred to above except that the cells were washed in 250 mM sucrose, 2 mM ethyleneglycol bis($\beta$-aminoethylether)-N,N,N',N' (EGTA), 10 mM Tris-HCl (pH 7.4). Adipocytes were resuspended in 20 ml of the above buffer and homogenised by aspirating through a Swinny filter at least 10 times. The cell homogenate was then centrifuged at 300 g for 5 min, the fat cake removed from the surface and the remaining pellet and infranatant transferred to clean tubes. These were centrifuged at 30,000 g for 1 h at 4° C. and the membrane pellet formed was resuspended in the sucrose buffer (200 to 400 $\mu$l). Plasma membranes were separated from other organelle membranes on a self-forming gradient of Percoll™ colloidial silica particles. The constituents were 250 mM sucrose, 2 mM EGTA, 10 mM Tris-HCl, pH 7.4; Percoll™; and 2M sucrose, 8 mM EGTA, 80 nM Tris-HCl, pH 7.4, mixed in a ratio of 32:7:1 together with the membrane suspension (in a total volume of 8 ml). This mixture was centrifuged at 10,000 g for 30 min at 4° C. The gradient was fractionated into 0.75 ml portions and each portion was assayed for the presence of succinate dehydrogenase, NADH-cytochrome c reductase, lactate dehydrogenase and 5'-nucleotidase to locate the plasma membrane fraction. The membrane fractions were resuspended in 150 mM NaCl, 1 mM EGTA, 10 mM Tris-HCl, pH 7.4 and centrifuged at 10,000 g at 4° C. for 2 min. The process was repeated twice. The washed plasma membranes were then diluted in 10 mM Tris-HCl, pH 7.4, 250 mM sucrose, 2 mM EGTA and 4 $\mu$M phenylmethylsulfonyl fluoride (PMSF) at 1–2 mg/ml, snap frozen in liquid nitrogen and stored at −70° C. until use.

Adenylate Cyclase Assay

An adenylate cyclase assay used was based on that developed by Salomon et al. (reference 16). Briefly, water (negative control), isoprenaline (positive control) or LMP was added to an assay mix (final volume 100 $\mu$l) containing 25 mM Tris-HCl, pH 7.5, 5 mM $MgCl_2$, GTP (guanine triphosphate), 8 mM creatine phosphate, 16 units/ml creatine phosphokinase, 1 mM 3-isobutyl-1-methylxanthine and 1 mM [$\alpha$-$^{32}$P] ATP (sp. act. 20 mCi/mmole). Preincubation was at 30° C. for 5 min and the reaction was initiated by the addition of plasma membrane (typically 50 $\mu$g protein). After 10 min at 30° C. the reaction was terminated by the addition of 100 $\mu$l of a solution containing 2% sodium dodecylsulphate, 40 mM ATP and 1.4 mM cyclic AMP. In order to determine recovery of cyclic AMP [8-$^3$H] adenosine 3',5'-cyclic phosphate (1 $\mu$Ci in 50 $\mu$l of water) was added to each tube. Background binding was determined by running samples without [$\alpha$-$^{32}$P] ATP and sample controls were set up without plasma membranes.

Samples containing labelled nucleotides were diluted to 1 ml with water and loaded onto Dowex™ 50W8-400 ion-exchange columns primed with 10 mM of water. After washing twice with 1 ml of water the cyclic AMP was eluted with 3 ml of water into polypropylene tubes containing 200 $\mu$l of 1.5M imidazole, pH 7.2. The samples were then applied to Alumina WN-3 columns (previously washed with 8 ml of 0.1M imidazole, pH 7.5) and the eluate collected directly into scintillation vials containing the scintillation fluid supplied under the Trade Mark Optiphase HiSafe 3. A further 1 ml of 0.1M imidazole was added to the columns and the eluate was combined with the run through. The radioactivity was determined using a Tri-carb™ 2000A scintillation analyser.

Zn-$\alpha_2$-glycoprotein

Samples of Zn-$\alpha_2$-glycoprotein were used in identifying the lipid mobilizing factor isolated. The Zn-$\alpha_2$-glycoprotein used was purified approximately 670-fold from fresh human plasma using a combination of DEAE-Sephadex A-50, DEAE-Sephacel, Zn-chelate Sepharose 6B, Phenyl-Sepharose, Sephacryl S-300 and HA-Ultrogel column chromatography substantially as described by Ohkubo et al. "Purification and characterisation of human plasma Zn-$\alpha_2$-glycoprotein" (1988) *Prep. Biochem* 18, 413–430 (reference 8), of which the content is incorporated herein by reference.

Gel Electrophoresis

Gels were prepared according to the method of Laemmli (reference 15) and generally consisted of a 5% stacking gel and a 15% SDS-PAGE resolving gel (denaturing or reducing conditions) or a 10% SDS-PAGE resolving gel (non-denaturing or non-reducing conditions). Samples were loaded at 1–5 $\mu$g/lane. Bands were visualised by staining either with Coomassie brilliant blue R-250 or by silver. Samples were prepared for reducing conditions by heating for 5 min at 100° C. in 0.0625M Tris-HCl, pH 6.8, 10% glycerol, 1% SDS, 0.01% bromophenol blue and 5% 2-mercaptoethanol.

For immunoblotting, the gels were transferred to nitrocellulose membranes which had been blocked with 5% Marvel in 0.15% Tween 20 in PBS at 4° C. overnight. The nitrocellulose membranes were washed once for 15 min and twice for 5 min in 0.5% Tween 20 in phosphate buffered saline (PBS) at room temperature. Immunodetection was carried out using polyclonal antiserum for Zn-$\alpha_2$-glycoprotein (10 $\mu$g/ml) prepared as described by Ohkubo et al. (see reference 8 mentioned above) in 1.5% Marvel, 0.15% Tween 20 in PBS for 1 hour at room temperature. After being washed three times as above the filters were incubated for 1 hour with protein A peroxidase conjugate at a 1:500-fold dilution followed by one 15 min wash and four 5 min washes with 0.5% Tween 20 in PBS. The ECL detection system was used, and the blots were suspended in equal volumes of detection reagents 1 and 2 using 0.125 ml/cm² for 1 min at room temperature and then wrapped in Saran Wrap™. The blots were exposed to autoradiography film (Hyperfilm™ ECL) for 30 seconds to 10 min depending on the amount of target protein.

BRIEF DESCRIPTION OF THE DRAWINGS

In connection with the description of the invention and illustrative examples detailed below reference should be made to the accompanying drawings in which:

FIG. 1 is a diagram of the complete amino acid sequence (SEQ ID No: 1) of the human plasma Zn-$\alpha_2$-glycoprotein, as published by T. Araki et al. (1988) "Complete amino acid sequence of human plasma Zn-$\alpha_2$-glycoprotein and its homology to histocompatibility antigens" (reference 4);

EXAMPLE 1

Figure 2:
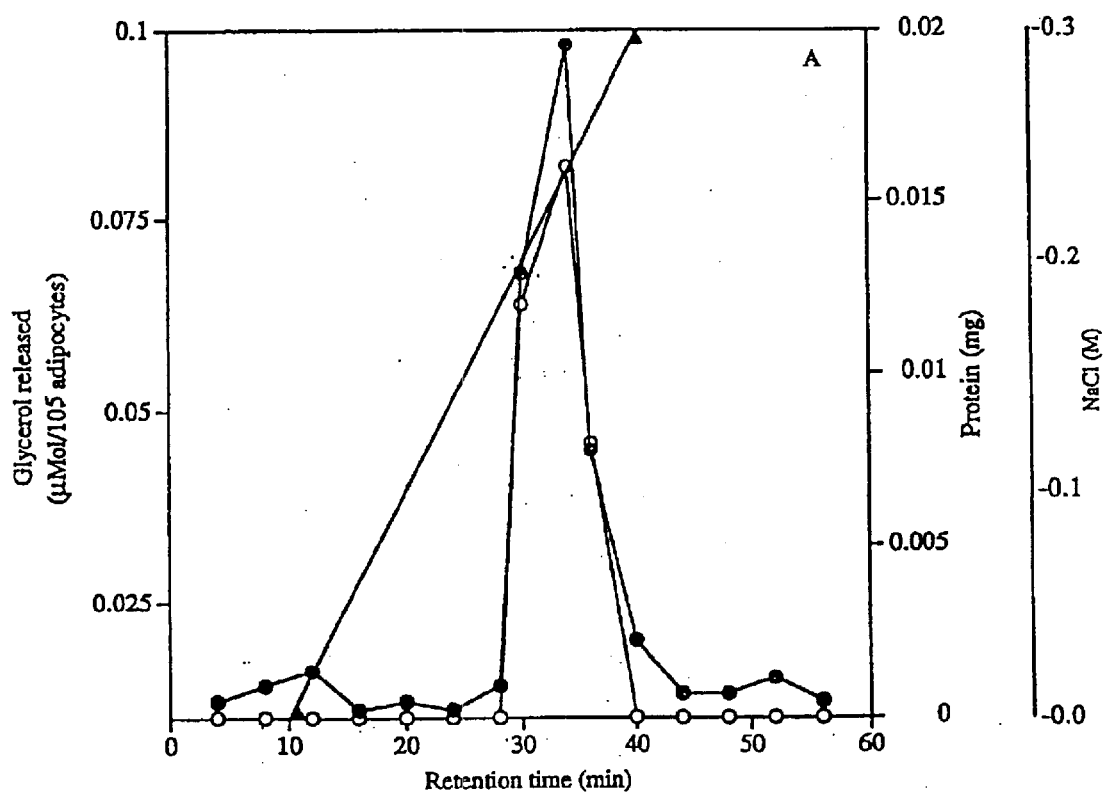
FIG. 2 is a diagram of the lipolytic activity distribution pattern and protein content of fractions obtained in a stage of anion exchange chromatography, using an Aquapore™ AX-300 DEAE column, applied to the active lipolytic fractions obtained from a preliminary stage of gel filtration chromatographic separation on a Q-Sepharose column as hereinafter described in Example 2.

Isolation and Purification of Lipid Mobilizing Factor from Murine Adenocarcinoma MAC16.

The procedure followed in this example is summarised in Table 1 at the end of the present description and involved the initial purification of the lipid mobilising factor (LMF) from the MAC16 tumour using a preliminary batch extraction on DEAE-cellulose and/or possibly protein precipitation by ammonium sulphate, followed by anion exchange chromatography on a Sepharose™ Mono Q HR 5/5 anion exchange column and size exclusion on Superose 12.

More particularly, solid tumours were excised from mice with weight loss and homogenized in 10 mM Tris-HCl (pH 8.0) containing 0.5 mM phenylmethylsulfonyl fluoride (PMSF), 0.5 mM EGTA, and 1 mM DTT at a concentration of 5 ml/g of tumour. Debris was removed from the homogenate by low-speed centrifugation (4000 rpm for 15 min in a bench-top centrifuge). When using ammonium sulfate precipitation, ammonium sulphate solution (38% w/v) was slowly added at this stage to the supernatant with stirring at 4° C. and the precipitate was removed by centrifugation (4500 rpm for 20 min). The supernatant was then concentrated using an Amicon filtration cell containing a membrane filter with a molecular weight cut-off of $M_r$ 10,000 against original homogenisation buffer.

Batch extraction on DEAE-cellulose at this stage was conveniently carried out substantially as described by T. M. McDevitt et al. "Purification and characterization of a lipid-mobilizing factor associated with cachexia inducing tumours in mice and humans" Cancer Res., (1995) 55, 1458–1463 (reference 1).

The next step was anion exchange chromatography using Q-Sepharose. The column used was the Mono Q HR 5/5 anion exchange column which has a protein capacity of 20–50 mg protein. The column was equilibrated prior to use with homogenising buffer, and the sample was loaded after centrifugation for 10 min at 1300 rpm as a 500-$\mu$l injection. After an initial wash, active material was eluted under a 0–0.2 M NaCl gradient. The presence of the active fractions was determined using the measurement of glycerol release from murine adipocytes in accordance with the lipolytic bioassay previously referred to. The active fractions were concentrated using an Amicon filtration cell and dissolved in 0.5 ml of 50 mM phosphate (pH 8.0) containing 0.3 M NaCl, 0.5 mM PMSF, 0.5 mM EGTA, and 1 mM DTT prior to FPLC Superose™ (or Superdex™) chromatography. The column used in carrying out this specific example was the Superose 12 prepacked 10/30 gel exclusion column, which was equilibrated with the above buffer for 2 hours at 0.25 ml/min, after which the sample was loaded as a 200-$\mu$l injection. Thirty 1.0 ml fractions were collected, and the lipid-mobilising activity was detected by the aforesaid lipolytic bioassay.

Up to this point the procedure has followed closely that described by McDevitt et al. in previously mentioned reference 9, but whereas the latter then continued with a final step of HPLC using a $C_8$ hydrophobic column and an acetonitrile/TFA gradient, in the present case the active fractions from the Superose column were further fractionated using an Aquapore™ AX-300 DEAE-cellulose column coupled to an HPLC system and eluting under a gradient from 0 to 0.3M NaCl before carrying out the final HPLC hydrophobic chromatography stage using the hydrophobic column marketed under the Trade Mark "Resource Iso". This modification led to the isolation of a much more stable bioactive product different from the products previously isolated.

In this last-mentioned stage of HPLC using the Aquapore™ AX-300 DEAE-cellulose column, typically the flow rate was 0.2 ml min$^{-1}$ with a solvent system composed of component A (10 mM Na-phosphate pH 5.3) and component B (10 mM Na-phosphate pH 5.3+0.3 M NaCl). All solvents were degassed prior to use. In one particular separation the gradient was changed according to the following protocol: 10 min 0%B, 40 minutes 100%B, 50 minutes 100%B, and 60 minutes 0%B. Absorbance ($A_{214}$) was monitored at 214 nm to determine protein content Each of the eluted peaks was collected as a separate fraction. The salt in these fractions from the DEAE-cellulose column was removed by ultrafiltration through a Microcon™ micro-concentrator containing a membrane filter having a molecular weight cut-off of $M_r$ 10,000 (Amicon) against deionized water containing 0.5 mM PMSF, 0.5 mM EGTA, 1 mM DTT. Again, the lipid-mobilising activity was detected by the lipolytic bioassay, and active fractions were concentrated using a Microcon™ microconcentrator against 50 mM phosphate buffer (pH 7.0) containing 1.5M ammonium sulfate prior to HPLC hydrophobic chromatography.

In the HPLC final step of this purification procedure using the hydrophobic column Resource™Iso, 1 ml (Pharmacia Biotech), the flow rate was 1 m/min$^{-1}$ with a solvent system C (50 mM phosphate pH 7.0+1.5 M ammonium sulfate) and D (50 mM phosphate pH 7.0). All solvents were degassed prior to use. A typical gradient protocol was 5 minutes 0%D, 20 minutes 100%D, 30 minutes 100%D, and 35 minutes 0%D. Again, absorbance ($A_{214}$) was monitored at 214 nm to determine protein content, and each of the eluted peaks was collected as a separate fraction. After removing the salt by ultrafiltration (through a Microcon™ microconcentrator against deionized water containing 0.5 mM PMSF, 0.5 mM EGTA, and 1 mM DTT) the lipid-mobilising activity was detected by the lipolytic bioassay as before.

EXAMPLE 2

Isolation and Purification of a Lipid-mobilising Factor from Urine of Cachectic Patients Urine from a cancer patient with weight loss was fractionated according to a scheme similar to that used for the MAC16 tumour, although fewer steps were required to get a pure product (see summary in Table 2 at the end of the present description) because of the lower protein content of urine. In the first stage the urine was subjected to precipitation with 80% $(NH_4)_2SO_4$ and the precipitate was dialysed against 10 mM Tris-HCl (pH 8.0) containing 0.5 mM PMSF, 0.5 mM EGTA and 10 mM DTT using an Amicon filtration cell containing a membrane filter having a molecular weight cut-off of $M_r$ 10,000. The urine concentrate was then fractionated by anion exchange chromatography using Q-Sepharose, followed by HPLC using an Aquapore™ AX-300 (30×21 mm) DEAE-cellulose column (flow rate of 0.2 ml min$^{-1}$ with 10 mM phosphate buffer at pH 5.3) under a linear 0–0.4M NaCl gradient which was run for 30 minutes. The protein content and the bioactivity of the fractions were determined respectively by measuring the absorbance $A_{214}$ and by measuring the release of glycerol from epididymal adipocytes using the standard lipolytic assay as previously described. The results of typical fractionation at this DEAE-cellulose fractionation stage are illustrated in the diagram of FIG. 2.

Figure 3:
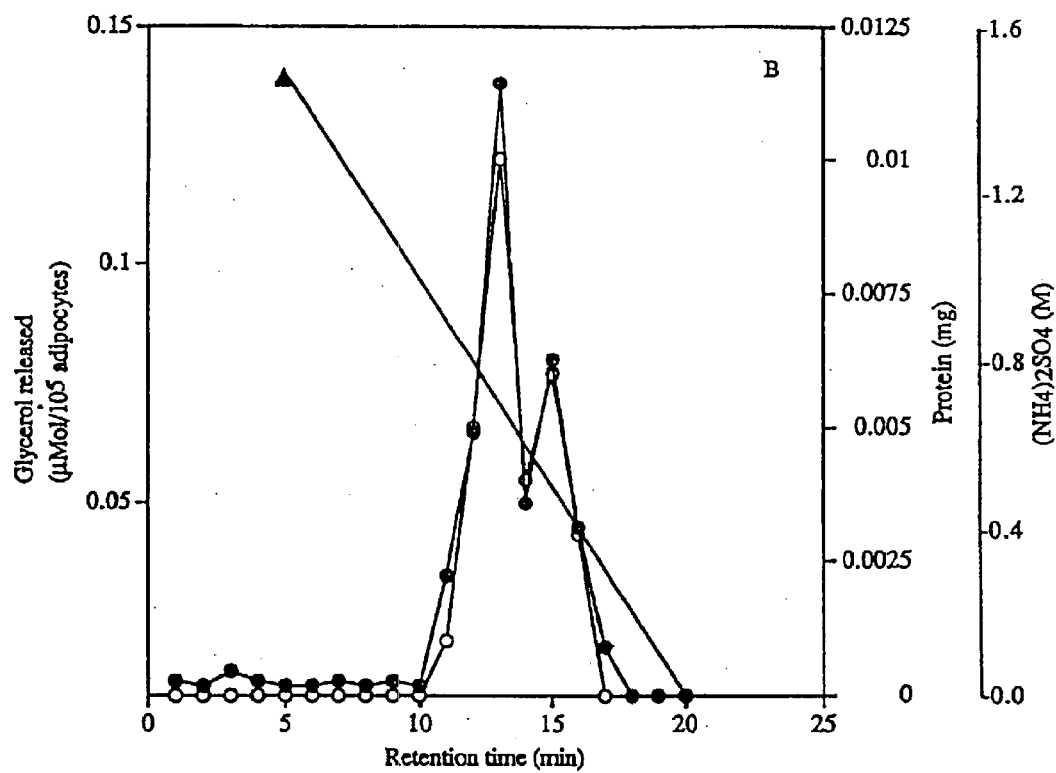
FIG. 3 is a diagram of the lipolytic activity distribution pattern and protein content of fractions obtained by a further stage of HPLC hydrophobic interaction chromatography on a Resource™ Iso hydrophobic column of those fractions from the Aquapore™ AX-300 DEAE fractionation stage illustrated in FIG. 2 that contained the major activity peak.

There then followed a final stage of hydrophobic interaction chromatography using the hydrophobic column Resource™Iso (6.4×30 mm) to fractionate the active material obtained from the DEAE-cellulose column, substantially as described in connection with Example 1. In this final stage, typically the starting buffer was 50 mM phosphate, pH 7.0, containing 1.5M $(NH_4)_2SO_4$ and the column was run under a linear gradient of the elution buffer (50 mM phosphate, pH 7.0, with a flow rate of 1 ml min$^{-1}$). The diagram of FIG. 3 illustrates the results in one example of this final stage of hydrophobic chromatography.

Upon repeating the procedure of Example 2 on a range of cancer patients and normal subjects it was found that although cancer patients with weight loss generally show the presence of this LMF in the urine it was absent from the urine of cancer patients without weight loss and from normal subjects, as demonstrated for example in Table 3 at the end of the present description.

Properties and Identity of the Lipid-Mobilising Factor (LMF) as Isolated in Examples 1 and 2

A. Molecular Weight

Figure 4:
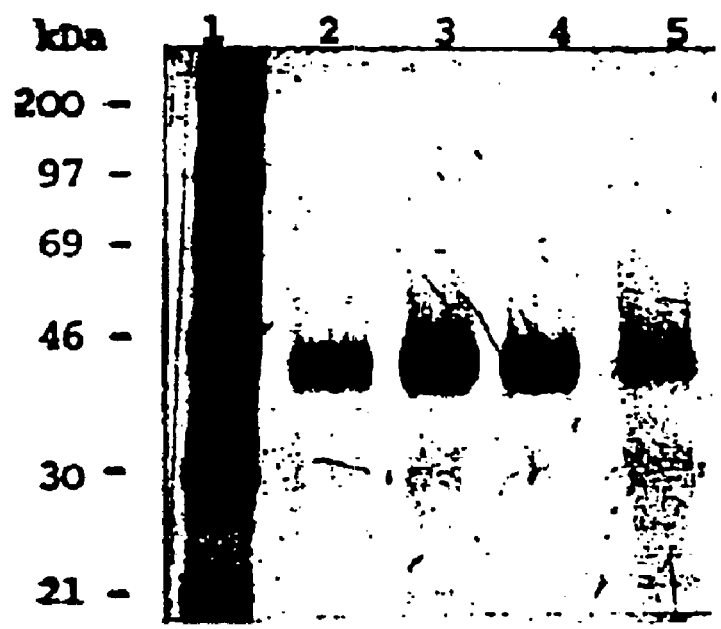
FIG. 4 shows the electrophoresis patterns produced by human and mouse LMF isolated and purified as in Examples 1 and 2, and also the pattern produced by human plasma Zn-$\alpha_2$-glycoprotein following 15% SDS-PAGE.

When subjected to 15% SDS-PAGE, both the human and mouse LMF, isolated and purified as described, showed a single protein band of an apparent relative molecular mass of $M_r$ 43 kDa. This is illustrated in FIG. 4 in which lane 1 shows molecular weight markers, lanes 3 and 4 show the banding pattern obtained with the human LMF and lane 5 shows the banding pattern obtained with the mouse LMF.

Figure 5:
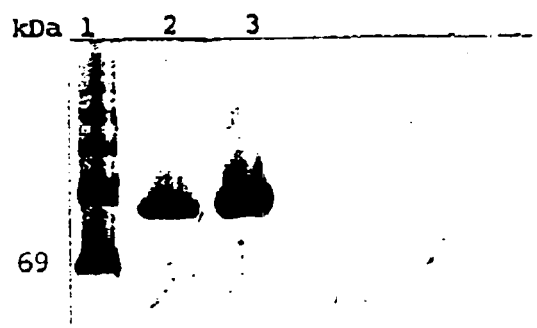
FIG. 5 is a diagram similar to FIG. 4 but shows the banding pattern obtained for human plasma Zn-$\alpha_2$-glycoprotein (lane 2) and for human LMF (lane 3) as prepared from Example 2.

When electrophoresed on 10% non-denaturing PAGE the purified human and mouse LMF both showed an apparent molecular weight of 84 kDa, the banding pattern obtained using the human LMF being shown in lane 3 of FIG. 5 wherein lane 1 again shows molecular weight markers.

B. Structure and Comparison with Zn-$\alpha_2$-glycoprotein

Sequence analysis of both the human and mouse LMF material revealed that it comprised a polypeptide chain having an N-terminus blocked by a pyroglutamate residue. Treatment with HCl or pyroglutamate aminopeptidase to remove this residue, or cleavage with chymotrypsin, produced peptides that showed homology with human plasma Zn-$\alpha_2$-glycoprotein in residues 2–6, 55–79 and 146–167 (see Araki et al., reference 4). Purified human and mouse LMF also comigrated with Zn-$\alpha_2$-glycoprotein when electrophoresed on 15% SDS-PAGE as illustrated in FIG. 4 in which lane 2 shows the banding pattern obtained using authentic human Zn-$\alpha_2$-glycoprotein (prepared as described in reference 8). The purified human LMF and human Zn-$\alpha_2$-glycoprotein also had the same molecular weight (84,000) on 10% non-denaturing PAGE (see lanes 3 and 2 respectively in FIG. 5). Using SDS-PAGE for detection of carbohydrate, both human and mouse materials stained heavily as did also authentic human Zn-$\alpha_2$-glycoprotein.

Figure 6:
FIG. 6 shows further banding patterns obtained with SDS-PAGE used for detecting carbohydrate as is also hereinafter described.

This is illustrated in FIG. 6 in which lane 1 shows the effect of human plasma Zn-$\alpha_2$-glycoprotein; lane 2 the effect of human LMF; lanes 3 and 4 the results with mouse LMF; lane 5 the result with transferrin (positive control); lane 6 the result with creatinase (negative control). The gel was stained for carbohydrate using the DIG glycan detection kit according to the manufacturer's instructions.

Figure 7:
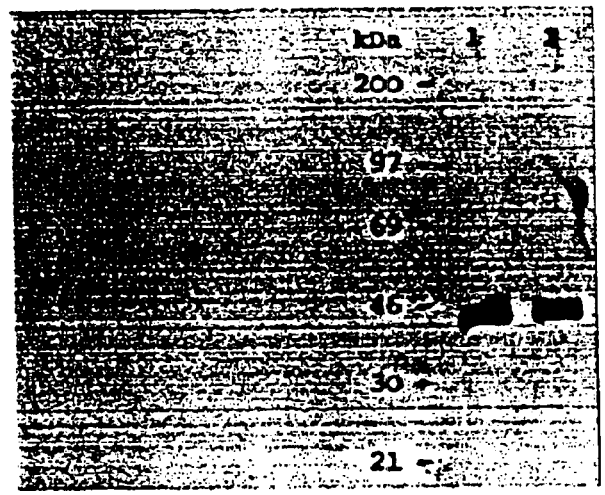
FIG. 7 shows a Western blot banding pattern produced by human plasma Zn-$\alpha_2$-glycoprotein (lane 1) and by human LMF (lane 2) after 15% SDS-PAGE using a polyclonal antibody to Zn-$\alpha_2$-glycoprotein.

It was also found that a polyclonal antibody raised against authentic human plasma Zn-$\alpha_2$-glycoprotein was capable of detection of human LMF on immunoblots, as shown in FIG. 7, and of neutralisation of in vitro lipid mobilizing activity of the human, but not the mouse material. The latter is indicated in Table 4, and an explanation of this observation may lie in the fact that mouse Zn-$\alpha_2$-glycoprotein has been shown to exhibit only 58.6% identity in amino acid sequence with the human counterpart (see reference 7).

Figure 8:
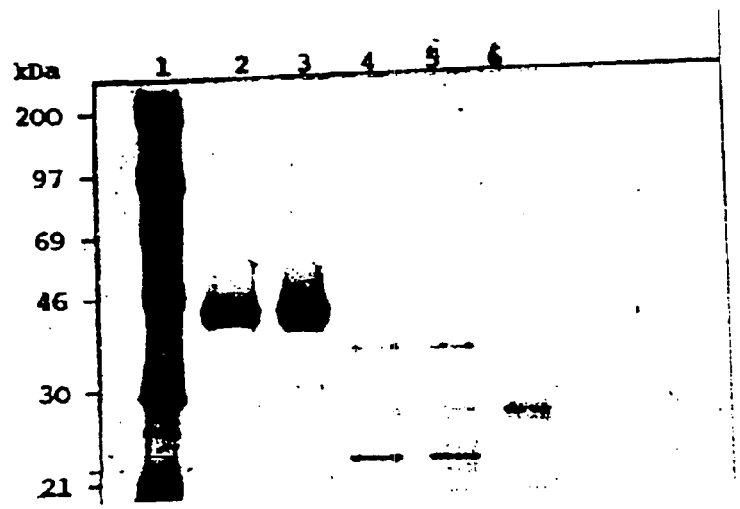
FIG. 8 is a further electrophoresis banding pattern obtained following experiments made to determine the effect of $\alpha$-chymotrypsin on human plasma Zn-$\alpha_2$-glycoprotein and on the isolated and purified human LMF.

FIG. 8 shows the effect of $\alpha$-chymotrypsin on authentic human plasma Zn-$\alpha_2$-glycoprotein and LMP. Lane 1 shows molecular weight markers; lane 2 shows human plasma Zn-$\alpha_2$-glycoprotein; lane 3 shows human LMF; lane 4 shows the result of Zn-$\alpha_2$-glycoprotein+$\alpha$-chymotrypsin; lane 5 represents human LMF+$\alpha$-chymotrypsin; and lane 6 is $\alpha$-chymotrypsin alone (control). Proteins were electrophoresed on 15% SDS-PAGE and stained with Coomassie brilliant blue. Both human plasma Zn-$\alpha_2$-glycoprotein and the isolated and purified LMF showed the same chymotryptic cleavage fragments and chymotrypsin destroyed the in vitro biological activity of the LMF. Neither human plasma Zn-$\alpha_2$-glycoprotein nor the human LMF contained the $M_r$ 24 kDa proteolysis inducing factor (PIF) previously reported to co-purify with the LMF.

The expression of Zn-$\alpha_2$-glycoprotein in various murine tumours and liver has also been quantitated by competitive PCR. Liver, being known to express Zn-$\alpha_2$-glycoprotein, was used as a control for the tumours. Of the MAC tumours evaluated only the cachexia-inducing MAC16 was found to express Zn-$\alpha_2$-glycoprotein.

C. Biological Activity

C.1 In vitro

Figure 9:
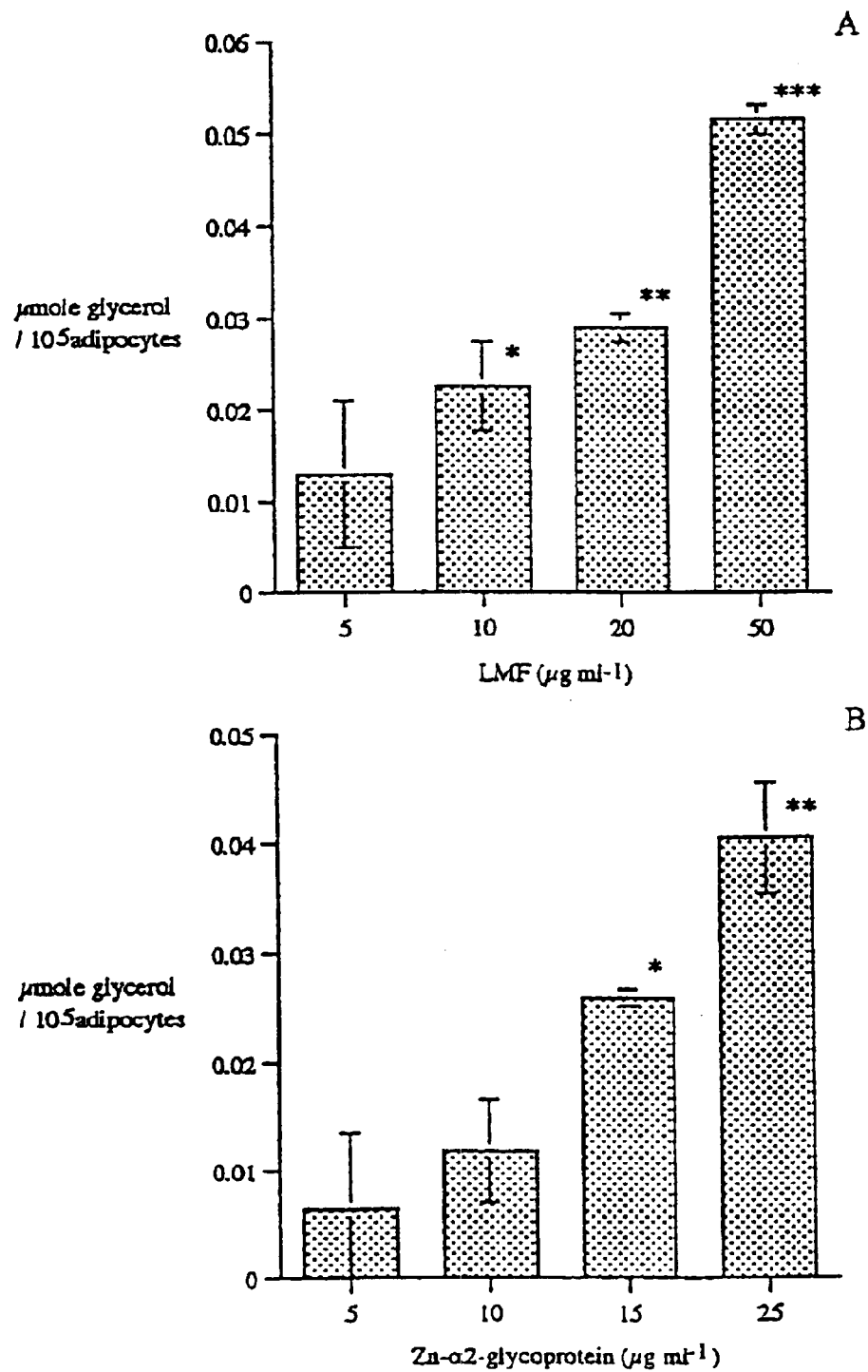
FIG. 9 is a bar chart diagram comparing the stimulation of lipolysis in freshly isolated murine epididymal adipocytes by human LMF (A) and by human Zn-$\alpha_2$-glycoprotein (B), the results being expressed as a mean±SEM Values for glycerol release from fat cells alone have been subtracted from the values given, and the data is representative of three separate experiments. Differences from controls were determined by Student's t-test and are indicated as *p$\leq$0.05, p$\leq$0.01 and *p$\leq$0.005.

The human LMF material isolated from the urine of cancer patients with weight loss as in Example 2 was tested at different doses for its lipolysis stimulating effect on freshly isolated murine epididymal adipocytes by measuring glycerol release using the lipolytic assay previously described. The test was also repeated using authentic human plasma Zn-$\alpha_2$-glycoprotein and it was found that both the authentic Zn-$\alpha_2$-glycoprotein and the human LMF material stimulated glycerol release with a comparable dose-response profile. This is illustrated in FIG. 9 where diagram A shows the results for the human LMF at different concentrations and diagram B shows the results for the authentic human plasma Zn-$\alpha_2$-glycoprotein.

Induction of lipolysis in adipocytes is thought to be mediated by an elevation of the intracellular mediator cyclic AMP, and in further tests it was found that incubation of murine adipocyte plasma membranes with the human LMF caused a stimulation of adenylate cyclase activity in a GTP-dependent process, with maximal stimulation occurring at 0.1 $\mu$M GTP. Also, this activation of adenylate cyclase was found to be saturable with concentrations of LMF >5 $\mu$g/assay. Using human plasma Zn-$\alpha_2$-glycoprotein it was found that this also stimulated murine adipocyte plasma membrane adenylate cyclase in a GTP-dependent manner with maximal stimulation also at 0.1 $\mu$M GTP. Again, this activation of adenylate cyclase by the Zn-$\alpha_2$-glycoprotein was found to be saturable with concentrations >5 $\mu$g/assay.

This data showing the similar effects and comparable dose-response profiles for LMF and Zn-$\alpha_2$-glycoprotein, together with the ability of polyclonal antisera to Zn-$\alpha_2$-glycoprotein to neutralise in vitro lipolysis by human LMF, the homology in amino acid sequence, and matching electrophoretic mobility, all provide strong evidence that the isolated and purified LMF is indeed Zn-$\alpha_2$-glycoprotein. Although previous reports have shown that Zn-$\alpha_2$-glycoprotein is an adhesive protein closely related to antigens of the major histocompatibility complex in amino acid sequence and domain structure, there have been no previous reports of a capacity of Zn-$\alpha_2$-glycoprotein to induce lipolysis. Moreover, it has not previously been reported as being present in human urine. At present the mechanism by which a large acidic protein such as Zn-$\alpha_2$-glycoprotein can stimulate adenylate cyclase is not known and is quite surprising since other known substances having a similar role are small and basic polypeptides.

C.2 In vivo

Figure 10:
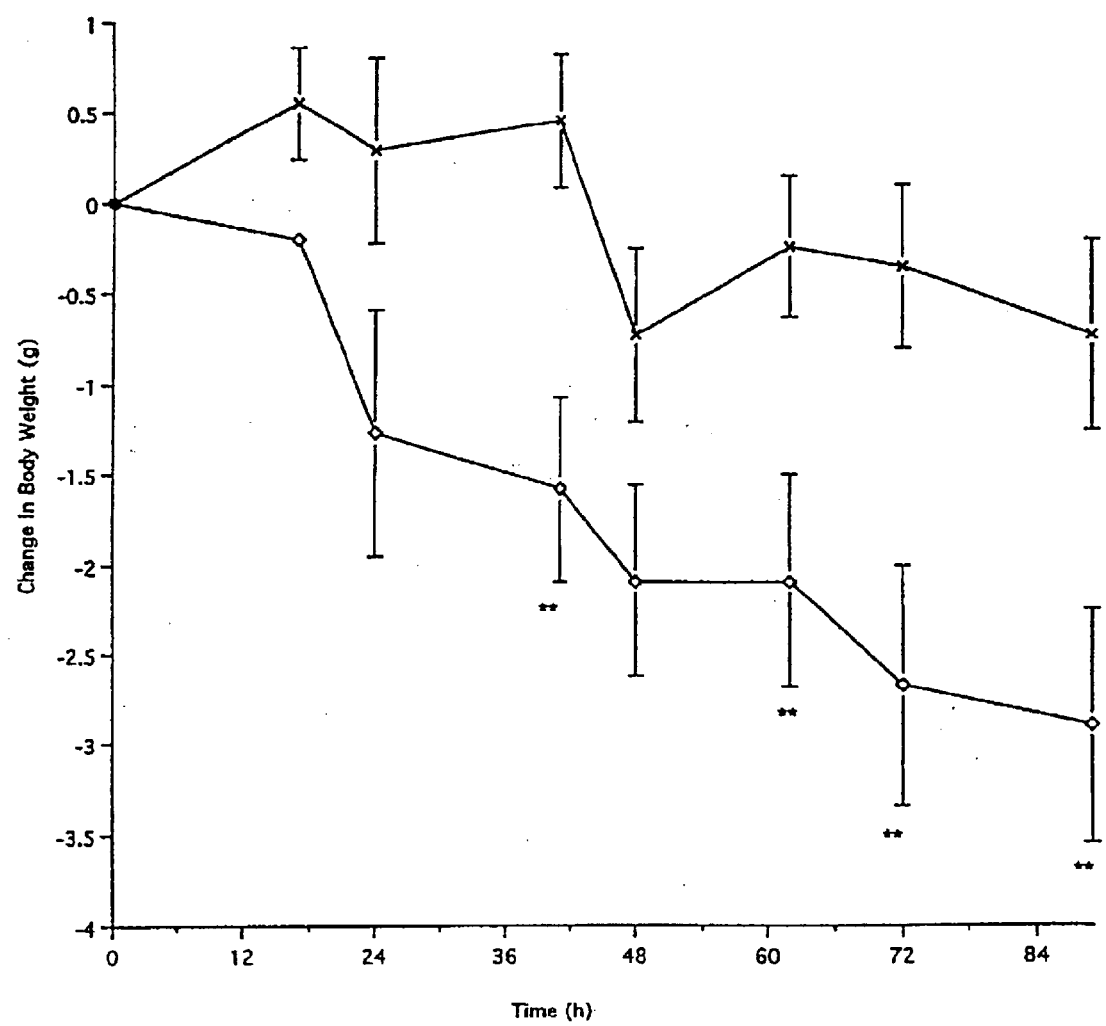
FIG. 10 is a diagram showing change in body weight of ex-breeder male NMRI mice (30–40 g) produced by intravenous (iv) administration of LMF (8 $\mu$g) isolated from human urine as described in Example 2 (o) and of control mice administered PBS by iv injection (x).

In order to determine if the purified LMF isolated from human urine as in Example 2 was capable of fat depletion in vivo a sample of this LMF material (8 $\mu$g) was injected into male ex breeder NMRI mice over a 72 h period. The LMF was injected at times 0, 17, 24, 41, 48, 62 and 72 hours and control mice were similarly injected with phosphate-buffered saline (PBS) at the same time points. The animals were killed at 89 h and the body composition and serum metabolite levels were determined. As shown in FIG. 10, there was a progressive decrease in body weight of the animals receiving LMF which was significantly lower than PBS treated controls within 41 h of treatment. Changes in the body composition and serum metabolic levels are summarised in Table 5 and it will be seen that total body weight decreased by 3.6 g during the overall 89 h period of the experiment without change in food and water intake. Body composition analysis showed a large reduction (42%) in the body fat content of mice receiving LMF, with a tendency to increase the non-fat mass although this did not reach a particularly significant level. In this connection some evidence has in fact been found indicating that the LMF may actually stimulate protein synthesis and thus increase muscle mass. Despite the fat mobilisation there were significant reductions in the serum concentrations of non-esterified fatty acids (NEFA), glycerol and glucose in mice receiving LMF.

Figure 11:
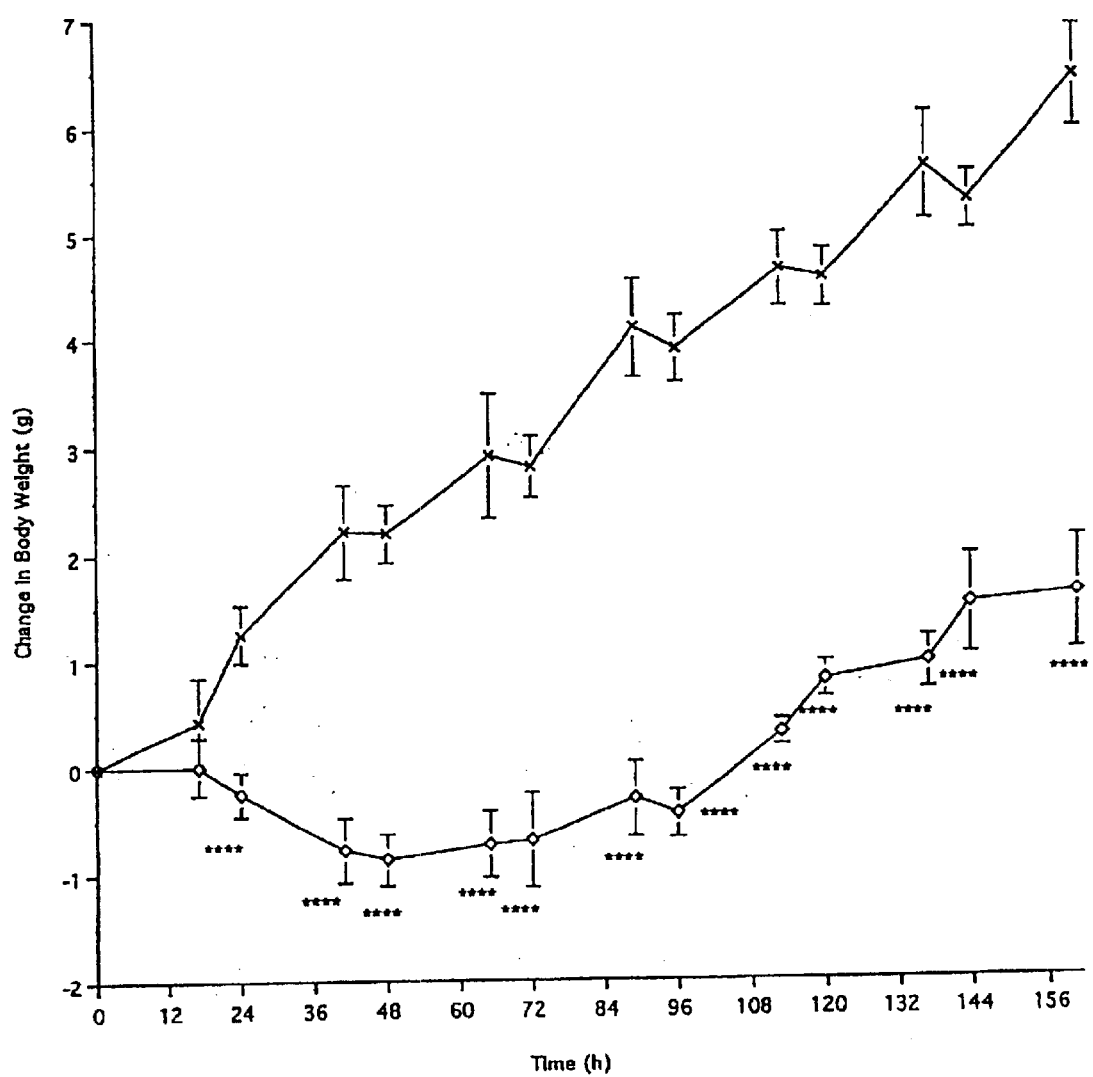
FIG. 11 is a diagram similar to FIG. 10 showing change in body weight of ob/ob mice produced by iv administration of LMF (35 $\mu$g) (o) isolated from human urine as described in Example 2 and of control mice (x) administered PBS by iv injection. LMF was injected at times 0, 16, 24, 40, 48, 64, 72, 90, 96, 113, 120, 137 and 144 h; PBS was injected at the same time points. The animals were killed 160 h after the first injection. Results are expressed as mean±SEM for 5 animals per group.

As shown in FIG. 11 and by the data in Table 6, intravenous administration to obese ob/ob mice of LMF (35 $\mu$g) isolated from human urine produced a similar result. There was a decrease in total body weight which became significant within 24 h of the first injection and remained below that of the control group over the 160 h of the experiment. Body composition analysis showed weight loss to arise from a decrease in carcass fat (26.03±0.70 g in controls and 21.09±0.99 g in LMF treated animals) without an alteration in the water content or non-fat mass (see Table 6). Serum levels of glycerol and 3-hydroxybutyrate were significantly increased, while blood glucose levels were decreased and there was no effect on either triglyceride or NEFA levels.

D. Fragmentation

Figure 12:
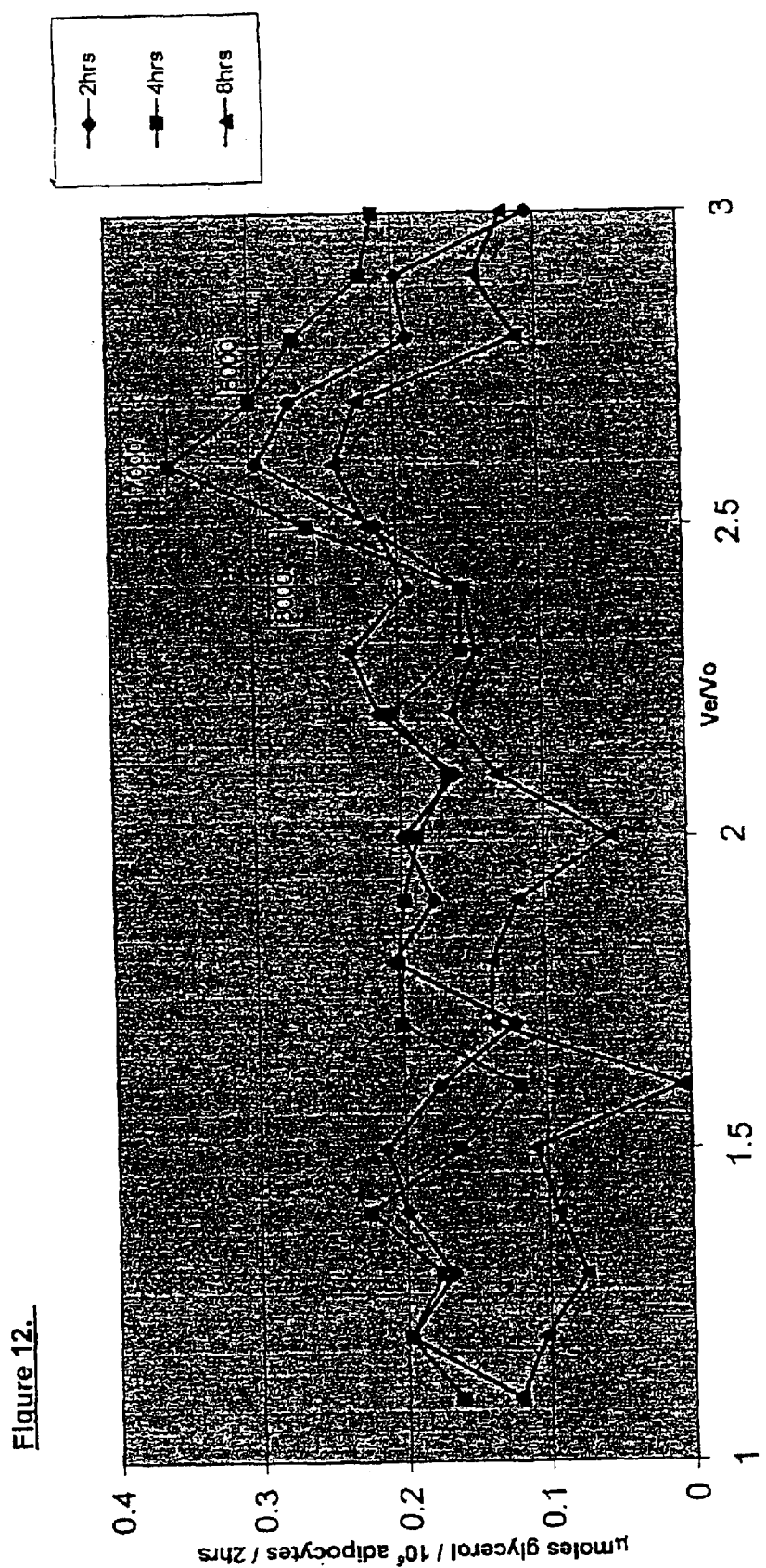
FIG. 12 shows graphs illustrating the effect of trypsin digestion for different time periods (2 hrs, 4 hrs and 8 hrs) on the biological activity of the 43 kDa LMF.

It was also established that the active 43 kDa glycoprotein could be digested with trypsin to give a fragment of apparent molecular weight or relative molecular mass of 7 kDa (as determined by gel filtration exclusion chromatography using a Sephadex™ 50 column) which still retains the biological activity of functioning as a lipid mobilising agent. This is illustrated by the results of a typical experiment depicted in FIG. 12 in which samples of the isolated human LMF were incubated with trypsin at 37° C. for different time periods and then analysed by Sephadex—50 Gel Exclusion Chromatography and lipolytic assay. The results clearly indicate the presence of active fragments within the 2.5 to 2.7 fractions, the M W of these fragments, as deduced from a calibration curve, being 6 kDa, 7 kDa and 8 kDa respectively as shown on the figure. Positive and negative controls were performed, these being as follows: −ve=0.027, +ve=0.252.

Therapeutic Use

Overall the results referred to in Section C.2 above in connection with the in vivo experiments confirmed an increased metabolism of fat and showed that in these model systems the isolated and purified human LMF produces a decrease in carcass weight specifically by depletion of adipose tissue. It is this particular ability of the human LMF, which is the same as or a close analogue of Zn-$\alpha_2$-glycoprotein, to reduce adipose tissue without affecting muscle mass that most clearly demonstrates the potential for use of this material for the treatment of obesity in humans. As has been mentioned earlier, there is also some evidence indicating that this LMF material can actually stimulate protein synthesis and may therefore be useful for stimulating muscle development Potentially, the material is also especially useful for treating humans with increased susceptibility to maturity onset diabetes such as can occur in cases of obesity.

For this therapeutic use, particularly for the controlled treatment of obesity in humans, either for medical reasons or cosmetic reasons, a therapeutically useful and non-toxic quantity of the essentially pure active substance, either a lipid mobilising factor isolated and purified substantially as herein described or the equivalent purified or synthetic Zn-$\alpha_2$-glycoprotein, or material constituting a lipolytically active fragment derived from the latter, can be made up as a pharmaceutical formulation for administration in any suitable manner. Such formulations may be presented in unit dosage form and may comprise a pharmaceutical composition, prepared by any of the methods well known in the art of pharmacy, in which a preparation of the active lipolytic substance is combined in intimate association or admixture with any other suitable ingredient providing a compatible pharmaceutically acceptable carrier, diluent or excipient. The formulations include those suitable for oral, rectal, topical and parenteral (including subcutaneous, intramuscular and intravenous) administration. For parenteral administration the formulations may comprise sterile liquid preparations of a predetermined amount of the active lipolytic substance contained in ampoules ready for use.

Formulations of the present invention suitable for oral administration may be presented as discrete units such as capsules, cachets, tablets or lozenges, each containing a predetermined amount of the active compound in the form of a powder or granules; or as a suspension of the active compound in an aqueous liquid or non-aqueous liquid such as a syrup, an elixir, an emulsion of a draught. The active compound may also be presented as a bolus, electuary or paste.

The amount of the active compound which is required in order to be effective for treating obesity in mammals will of course vary and is ultimately at the discretion of the medical or veterinary practitioner treating the mammal in each particular case. The factors to be considered by such practitioner, e.g. a physician, include the route of administration; type of pharmaceutical formulation; the mammal's body weight, surface area, age and general condition.

Diagnostic Applications

For diagnostic purposes, to detect the presence of a tumour in a human patient or to monitor the progress of a tumour under treatment, basically it is only necessary simply to take a sample of body fluid such as urine in which Zn-$\alpha_2$-glycoprotein is not normally present in healthy individuals, and then to test this for the presence of the glycoprotein lipid mobilising agent or lipolytic factor (or equivalent Zn-$\alpha_2$-glycoprotein) herein identified.

In practice, any convenient method may be used for detecting and/or measuring this active lipid mobilising agent or lipolytic factor in the samples, and the apparatus and materials required may advantageously be packaged and supplied, together with appropriate practical instructions, in the form of self-contained diagnostic kits ready for immediate use. Particularly preferred diagnostic agents for detecting and/or measuring the active lipid mobilising or lipolytic factor in a convenient and reliable manner are biochemical reagents, such as monoclonal or polyclonal antibodies for example, capable of specifically recognising and binding to human Zn-$\alpha_2$-glycoprotein and then being identifiable by, for example, a visual change or a special screening using an associated labelled marker molecule, or by any other suitable technique known in the art.

Monoclonal Antibodies

The production of monoclonal antibodies to the Zn-$\alpha_2$-glycoprotein or Zn-$\alpha_2$-glycoprotein like lipolytic factor of this invention can be achieved by the use of established conventional techniques commonly used in the art Such monoclonal antibodies, once prepared, may be immobilized on suitable solid supports (in a column for example) and then used for affinity purification to prepare in a convenient manner any further quantities that may be required for testing of the purified active lipolytic factor from tumour extracts or body fluids.

It is envisaged, however, that another important use of such monoclonal antibodies, apart from their use as a diagnostic agent, will be a therapeutic application based on their properties as inhibitors or antagonists to the active lipolytic factor in human cancer patients and a consequent therapeutic value as agents for treating and suppressing the symptoms of cachexia and/or for preventing or reducing tumour growth. Thus, by virtue of this property, they can provide therapeutic agents and, more specifically, they can be used to make or manufacture a medical preparation or medicament for the therapeutic treatment of cancer-associated cachexia and/or malignant tumours in mammals.

Screening Applications

Apart from monoclonal antibodies as referred to above, it is likely that any agent which is antagonistic to, or an inhibitor of, the activity of this lipid mobilising or lipolytic factor of the present invention could have at least potential human therapeutic value. Hence, preparations of the purified, or at least partially purified, lipolytic factor (LMF) herein identified can be particularly useful, in accordance with a further aspect of the invention, for use in providing a convenient in vitro method of screening substances to find potential anti-cachectic and/or antitumour agents for therapeutic use. A typical example of this application using freshly prepared adipocytes from mouse epididymal adipose tissue is outlined below:

The experiments are set up as follows:

100 µl purified LMF preparation+1 ml fat cells

Compound to be screened+1 ml fat cells

100 µl LMF preparation and compound+1 ml fat cells

Each compound is tested at increasing concentrations and all samples are prepared and processed in duplicate.

The samples are gassed for 2 min with 95% $O_2$, 5% $CO_2$ mixture, mixed and incubated for 2 hour at 37° C. After 2 hour, 0.5 ml from each sample is then assayed for glycerol content as hereinbefore described.

Compounds which appear to show some significant degree of inhibition can then be candidates for further evaluation.

In general, the inhibitory effect observed in such in vitro experiments can be expected to occur also in vivo, and it is anticipated that by using this screening method further antagonists or inhibitors will be found that will have useful therapeutic applications for the treatment of cancer-associated cachexia and/or as antitumour agents.

MAC16 Cell Line and Purification

Although it is quite feasible for preparations containing useful amounts of the purified or partially purified active lipid mobilising or lipolytic factor to be produced as herein described from extracts of tumours, such as the MAC16 adenocarcinoma, grown in vivo, or from urine of cancer cachexia patients, or by synthetic methods, a more convenient and preferred alternative source may be provided by extracts of tumour tissue cell cultures, especially cultures of the MAC16 cell line previously referred to.

The cells of this cell line can be conveniently grown in RPMI 1640 media containing 10% foetal calf serum under an atmosphere of 10% $CO_2$ in air. When assayed in the adipocyte glycerol release assay method it has been found that such culture grown cells may release a greater amount of glycerol than do corresponding amounts of the tumour in vivo.

As will be seen, the invention presents a number of different aspects and it should be understood that it embraces within its scope all novel and inventive features and aspects herein disclosed, either explicitly or implicitly and either singly or in combination with one another. Also, many detail modifications are possible and, in particular, the scope of the invention is not to be construed as being limited by the illustrative example(s) or by the terms and expressions used herein merely in a descriptive or explanatory sense. It is also pointed out that insofar as the terms "lipid mobilising factor (LMF)", "lipid mobilising agent" and "lipolytic factor" are used in the present specification, these terms are generally to be regarded as being synonymous and have the same meaning.

TABLE 1

Purification of Lipid-Mobilizing Factor from MAC 16 tumor

| Purification stage | Total protein (mg) | Recovery (%) | Total activity ($\mu$mol/ $10^5$ adipocytes) | Recovery (%) | Specific activity ($\mu$mol/$10^5$ adipocytes/ mg protein) | Purification fold |
|---|---|---|---|---|---|---|
| Tumor homogenate | 500 | 100 | 27 | | 0.054 | |
| Batch extraction on DEAE-cellulose | 102 | 20.4 | 1.21 | 100 | 0.0119 | 1 |
| Q-Sepharose | 1.5 | 0.3 | 1.17 | 97 | 0.78 | 65 |
| Superdex | 0.61 | 0.1 | 1.12 | 93 | 1.84 | 154 |
| HPLC DEAE-cellulose | 0.12 | 0.02 | 1.02 | 84 | 8.5 | 714 |
| HPLC Resource-iso | 0.02 | 0.004 | 1 | 83 | 50 | 4201 |

TABLE 2

Purification of Lipid-Mobilizing Factor from Cancer Patient Urine

| Purification stage | Total protein (mg) | Recovery (%) | Total activity ($\mu$mol/ $10^5$ adipocytes) | Recovery (%) | Specific activity ($\mu$mol/$10^5$ adipocytes/ mg protein) | Purification fold |
|---|---|---|---|---|---|---|
| 80% $(NH_4)_2SO_4$ precipitation | 210 | 100 | 78.4 | | 0.37 | |
| Q-Sepharose | 0.2 | 0.1 | 1.19 | 100 | 5.95 | 1 |
| HPLC DEAE-cellulose | 0.036 | 0.017 | 1.15 | 97 | 31.9 | 5.4 |
| HPLC Resource-Iso | 0.007 | 0.003 | 1.15 | 97 | 164.3 | 27.8 |

TABLE 3

Relationship between weight loss and appearance of LMF in urine

| Patient number | Diagnosis | Weight loss (kg/month) | LMF |
|---|---|---|---|
| 1. | Pancreatic cancer | 1.6 | + |
| 2. | Chorangio carcinoma | 4.2 | + |
| 3. | Gastric cancer | 3.0 | + |
| 4. | Gastric cancer | 2.2 | − |
| 5. | Pancreatic cancer | 0 | − |
| 6. | Pancreatic cancer | 4.6 | + |
| 7. | Pancreatic cancer | 1.5 | + |
| 8. | Ovarian cancer | 4.3 | + |
| 9. | Rectal cancer | 0.7 | + |
| 10. | Periampullary cancer (recurrence) | 0.3 | + |
| 11. | Colorectal cancer | 0.5 | − |
| 12. | Hepatoma | 1.4 | + |
| 13. | Pancreatic cancer | 4.0 | + |
| 14. | Periampullary cancer | 0.8 | − |
| 15. | Pancreatic cancer | 1.3 | + |
| 16. | Normal | 0 | − |

TABLE 4

Effect of a polyclonal antibody to human Zn $\alpha_2$-glycoprotein on human and mouse lipid mobilizing activity.

| Addition | $\mu$mole glycerol/$10^5$ adipocytes/2h | p (from factor alone) |
|---|---|---|
| Human LMF | 0.0062 ± 0.0002 | |
| Human LMF + pAb | 0.0013 ± 0.0012 | 0.03 |
| Mouse LMF | 0.0977 ± 0.02 | |
| Mouse LMF + pAb | 0.1082 ± 0.015 | NS |

LMF (5 $\mu$g human or 10 $\mu$g mouse in PBS) were incubated overnight with agitation at 4° C. with a polyclonal antibody (pAb) to human plasma Zn-$\alpha_2$-glycoprotein (10 $\mu$g in PBS) and the lipid mobilizing activity was determined as described in methods.
Results are expressed as mean ± SEM for three determinations and the experiment was repeated three times.
Differences from values in the absence of the pAb were determined by Student's t-test.

TABLE 5

The effect of LMF isolated from human urine on body weight, body composition, food and water intake and serum metabolite levels in ex-breeder male NMRI mice

| Parameter | Control | Treated | P |
|---|---|---|---|
| Final body weight (g) | 35.5 ± 2.0 | 31.6 ± 2.2 | 0.01 |
| Water (g) | 22.0 ± 0.9 | 18.3 ± 0.8 | NS |
| Non Fat (g) | 7.7 ± 0.8 | 9.6 ± 0.9 | NS |
| Fat (g) | 5.9 ± 0.6 | 3.4 ± 0.4 | 0.05 |
| Food intake (g/day) | 8.0 ± 0.6 | 8.0 ± 0.2 | NS |
| Water intake (ml/day) | 4.5 ± 0.8 | 4.4 ± 0.4 | NS |
| NEFA (mEq/l) | 1.63 ± 0.09 | 0.95 ± 0.03 | 0.003 |
| Glycerol (mM) | 8.86 ± 0.51 | 6.73 ± 0.45 | 0.05 |
| Triglyceride (mg/l) | 0.323 ± 0.036 | 0.201 ± 0.027 | NS |
| Glucose (mg/100 ml) | 223 ± 9 | 186 ± 0.08 | 0.02 |

Material was administered to mice according to the schedule in FIG. 10.
Values represent the mean ± SEM for 5 mice per group.
Differences from control values were determined by Student's t-test.

TABLE 6

The effect of human LMF on body weight body composition, food and water intake and serum metabolite levels in ob/ob mice 160 h after the first injection.

| Parameter | Control | Treated | P |
|---|---|---|---|
| Initial body weight (g) | 66.7 ± 4.2 | 67.9 ± 2.9 | NS |
| Final body weight (g) | 73.1 ± 4.3 | 69.5 ± 4.3 | 0.01 |
| Water (%) | 50.3 ± 0.5 | 53.7 ± 1.1 | NS |
| Non Fat (%) | 15.5 ± 0.9 | 17.4 ± 1.0 | NS |
| Fat (%) | 34.6 ± 0.6 | 30.6 ± 0.7 | 0.05 |
| NEFA (mEq/l) | 1.47 ± 0.12 | 1.45 ± 0.45 | NS |
| Glycerol (mM) | 2.51 ± 0.28 | 5.31 ± 0.45 | 0.02 |
| Triglyceride (mg/l) | 0.40 ± 0.05 | 0.49 ± 0.04 | NS |
| Glucose (mg/100 ml) | 317 ± 11 | 260 ± 12 | 0.02 |
| 3-Hydroxybutyrate (mM) | 0.30 ± 0.02 | 0.44 ± 0.01 | 0.001 |
| Oxygen uptake ($\mu$l/mg BAT/h) | 0.18 ± 0.06 | 0.55 ± 0.07 | 0.009 |

Material was administered to mice according to the schedule in FIG. 11.
Values represent the mean ± SEM for 5 mice per group.
Differences from control values were determined by Student's t-test.

References (1) T. M. McDevitt et al., (1995) "Purification and characterisation of a lipid-mobilising factor associated with cachexia-inducing tumours in mice and humans", *Cancer Research* 55, 1458–1463.

(2) P. Todorov et al. (1996), Nature, 379, 739–742.

(3) Burgi and Schmid, (1961) "Preparation and properties of Zn-$\alpha_2$-glycoprotein of normal human plasma" *J. Biol. Chem.* 236, 1066–1074.

(4) T. Araki et al. (1988) "Complete amino acid sequence of human plasma Zn-$\alpha_2$-glycoprotein and its homology to histocompatibility antigens" *Proc. Natl. Acad. Sci. USA.*, 85, 679–683.

(5) H. Ueyama, et al. (1991) "Cloning and nucleotide sequence of a human Zn-$\alpha_2$-glycoprotein cDNA and chromosomal assignment of its gene", *Biochem. Biophys. Res. Commun.* 177, 696–703.

(6) H. Ueyama et al. (1993) "Molecular cloning and chromosomal assignment of the gene for human Zn-$\alpha_2$-glycoprotein", *Biochemistry* 32, 12968–12976.

(7) H. Ueyama et al. (1994) "Structure and Expression of Rat and Mouse mRNAs for Zn-$\alpha_2$-glycoprotein" *J. Biochem.*, 116, 677–681.

(8) Ohkubo et al. (1988) "Purification and characterisation of human plasma Zn-$\alpha_2$-glycoprotein" *Prep. Biochem.*, 18, 413–430.

(9) Kohler et al., (1976), *Eur. J. Immuno.*

(10) D. M. Weir, "*Handbook of Experimental Immunology*", 3, $2^{nd}$ ed. pp A2.10–A2.11, *Blackwell Scientific Publications, Oxford*, 1973.

(11) M. Z. Atassi and A. F. S. A. Habeeb, "*Immunochemistry of Proteins*" (M. Z. Atassi, ed), 2, pp 177–264, Plenum, New York, 1977.

(12) Lanoyi and Nisonoff (1983), J. Immuno. Meth., 56, 235.

(13) Wieland, O. (1974), in "*Methods of Enzymatic Analysis*" (Ed. Bergmeyer, H. U.) Vol. 3. pp 1404–1409, Academic Press, N.Y.

(14) S. A. Beck et al. (1987) "Production of lipolytic and proteolytic factors by a murine tumour-producing cachexia in the host" *Cancer Res.* 47, 5919–5923 (reference 14).

What is claimed is:

1. A method of treating a mammal to bring about a weigh reduction or reduction in obesity, said method comprising administering to the mammal in need of such treatment a therapeutically effective dosage of a lipid mobilizing agent which is a Zn-$\alpha_2$-glycoprotein, the polypeptide moiety thereof having the sequence as shown in SEQ ID NO:1.

2. A method of treating a mammal to bring about a weight reduction or reduction in obesity, said method comprising administering to the mammal in need of such treatment a therapeutically effective dosage of a lipid mobilizing agent having an apparent molecular mass of greater than about 6 kDa, as determined by gel exclusion chromatography, and which is obtained by digesting Zn-$\alpha_2$-glycoprotein, the polypeptide moiety of which has the sequence shown in SEQ ID NO:1, with the enzyme trypsin.

* * * * *

SEQUENCE LISTING

```
<160> NUMBER OF SEQ ID NOS: 1

<210> SEQ ID NO 1
<211> LENGTH: 276
<212> TYPE: PRT
<213> ORGANISM: Homo sapiens

<400> SEQUENCE: 1

Gln Glu Asn Gln Asp Gly Arg Tyr Ser Leu Thr Tyr Ile Tyr Thr Gly
 1               5                  10                  15

Leu Ser Lys His Val Glu Asp Val Pro Ala Phe Gln Ala Leu Gly Ser
                20                  25                  30

Leu Asn Asp Leu Gln Phe Phe Arg Tyr Asn Ser Lys Asp Arg Lys Ser
            35                  40                  45

Gln Pro Met Gly Leu Trp Arg Gln Val Glu Gly Met Glu Asp Trp Lys
        50                  55                  60

Glu Asp Ser Gln Leu Gln Lys Ala Arg Glu Asp Met Glu Thr Leu Lys
65                  70                  75                  80
```

-continued

```
Asp Ile Val Glu Tyr Tyr Asn Asp Ser Asn Gly Ser His Val Leu Gln
                 85                  90                  95
Gly Arg Phe Gly Cys Glu Ile Glu Asn Asn Arg Ser Ser Gly Ala Phe
            100                 105                 110
Trp Lys Tyr Tyr Tyr Asp Gly Lys Asp Tyr Ile Glu Phe Asn Lys Glu
        115                 120                 125
Ile Pro Ala Trp Val Pro Phe Asp Pro Ala Ala Gln Ile Thr Lys Gln
    130                 135                 140
Lys Trp Glu Ala Glu Pro Val Tyr Val Gln Arg Ala Lys Ala Tyr Leu
145                 150                 155                 160
Glu Glu Glu Cys Pro Ala Thr Leu Arg Lys Tyr Leu Lys Tyr Ser Lys
                165                 170                 175
Asn Ile Leu Asp Arg Gln Asp Pro Pro Ser Val Val Val Thr Ser His
            180                 185                 190
Gln Ala Pro Gly Glu Lys Lys Lys Leu Lys Cys Leu Ala Tyr Asp Phe
        195                 200                 205
Tyr Pro Gly Lys Ile Asp Val His Trp Thr Arg Ala Gly Gln Val Gln
    210                 215                 220
Glu Pro Glu Leu Arg Gly Asp Val Leu His Asn Gly Asn Gly Thr Tyr
225                 230                 235                 240
Gln Ser Trp Val Val Val Ala Val Pro Pro Gln Asp Thr Ala Pro Tyr
            245                 250                 255
Ser Cys His Val Gln His Ser Ser Leu Ala Gln Pro Leu Val Val Pro
            260                 265                 270
Trp Glu Ala Ser
            275
```